United States Patent [19]

Dell et al.

[11] Patent Number: 5,275,668
[45] Date of Patent: Jan. 4, 1994

[54] HYDRO IMPACT MEDICAL AND DENTAL INSTRUMENTS WASHER

[76] Inventors: Joseph G. Dell, R.R. 1, Box 228, Judith Dr., Stormville, N.Y. 12582; Robert A. Anderson, 3425 Hoag, Grand Rapids, Mich. 49503; Richard L. Despres, 0279 Luce, Grand Rapids, Mich. 49504

[21] Appl. No.: 859,634

[22] Filed: Mar. 20, 1992

Related U.S. Application Data

[63] Continuation-in-part of Ser. No. 569,630, Aug. 20, 1990, abandoned.

[51] Int. Cl.⁵ .................... B08B 7/04; B08B 3/00; C03C 23/00; A61L 2/00
[52] U.S. Cl. ........................... 134/10; 134/2; 134/186; 134/195; 422/300; 422/292
[58] Field of Search ............ 422/292, 300; 134/25.5, 134/105, 108, 34, 186, 191, 195, 22.1, 22.11, 22.12, 22.18, 10, 2

[56] References Cited

U.S. PATENT DOCUMENTS

| | | | |
|---|---|---|---|
| 2,054,366 | 9/1936 | Drake | 422/300 X |
| 2,619,099 | 11/1952 | Young | 422/300 X |
| 3,101,728 | 8/1963 | Broge | 134/108 X |
| 3,478,758 | 11/1969 | Davies | 422/300 X |
| 3,991,779 | 11/1976 | Saurenman | 422/28 X |
| 4,097,235 | 6/1978 | Stock | 422/300 X |
| 4,410,492 | 10/1983 | Kaye | 422/27 |
| 4,526,623 | 7/1985 | Ishii et al. | 134/34 X |
| 4,552,163 | 11/1985 | Biancalana et al. | 134/100 |
| 4,740,249 | 4/1988 | McConnell | 134/25.5 X |
| 4,801,333 | 1/1989 | Mosel | 134/186 X |
| 4,938,257 | 7/1990 | Morris | 134/108 X |
| 5,039,349 | 8/1991 | Schoeppel | 134/108 X |
| 5,090,433 | 2/1992 | Kamaga | 134/169 C |
| 5,127,424 | 7/1992 | Stein et al. | 134/186 X |

Primary Examiner—Robert J. Warden
Assistant Examiner—Christopher Y. Kim
Attorney, Agent, or Firm—Heslin & Rothenberg

[57] ABSTRACT

A medical and dental instruments washer is capable of washing medical and dental instruments clean within a few minutes. The washer contains a watertight chamber with a means for holding the instruments. A pump recirculates the cleaning solution within the chamber at a velocity and flow rate which is sufficient to wash the instruments.

23 Claims, 7 Drawing Sheets

HYDRO IMPACT MEDICAL AND DENTAL INSTRUMENTS WASHER

This application is a continuation-in-part of U.S. Ser. No. 569,630, filed Aug. 20, 1990, the contents of which are incorporated by reference into the subject application.

BACKGROUND OF THE INVENTION

The present invention relates to the field of medical and dental instrument cleaning, and more particularly, to a hydro impact medical and dental instruments and other armamentarium washer.

In the conventional technique of cleaning medical and dental instruments, the instruments are first hand scrubbed using brushes with detergent and water. Subsequently, the instruments are placed in an ultrasonic cleaner designed to clean instruments using an ultrasonic solution and action. After the instruments are removed from the ultrasonic cleaner, they are placed in an autoclave or other sterilizing device. After these three steps, the instruments are considered sterile and reusable on other patients.

The problem with the conventional process, however, is that it is inefficient, labor intensive., hazardous, and expensive. The ultrasonic cleaner is designed to clean medical and dental instruments without preliminary hand scrubbing. However, this device has been ineffective in cleaning medical and dental instruments so that 100% of the residual material (human tissue, chemicals, medications, etc.) is removed. As a result, it has been necessary to hand scrub the instruments prior to placing them in the ultrasonic cleaner.

There are several disadvantages to hand scrubbing the instruments. The burden on office staff is increased because of the additional labor time required to scrub the instruments. Also, certain instruments are extremely sharp and may contain fine points conducive to puncture or cutting of the skin thereby making scrubbing of the instruments very dangerous. Office personnel are reluctant to hand scrub medical and dental instruments partly because there is an increase in awareness of the possibility of diseases transmitted from patients through contaminated equipment. Furthermore, hand scrubbing of the contaminated instruments may produce a splattering of contaminants with the splashing of water which causes office personnel to be concerned about disease transmission. Finally, hand scrubbing increases office expenses because it is extremely time consuming and inefficient. To properly remove 100% of the residual contaminants left on medical and dental instruments, a person must spend an extensive amount of time hand scrubbing. Accordingly, it is highly desirable to eliminate all hand scrubbing of contaminated medical and dental instruments.

Another disadvantage with the present system is that the ultrasonic cleaners use expensive hazardous ultrasonic solutions which generate hazardous wastes. Elimination of the use of these ultrasonic solutions would eliminate the handling and disposal of hazardous waste and decrease costs associated with the purchase of these expensive solutions. After ultrasonic cleaning, the instruments should be 100% clean of all contaminants for proper sterilization of the instruments. However, since instruments are often not completely clean when they are removed from the ultrasonic cleaner, residue material and other contaminants remain on the instruments even after they are removed from the autoclave or other sterilization device. Because of the inefficiency of the ultrasonic cleaners, tissue residue and other contaminants often remain on the medical and dental instruments prior to their insertion into the sterilizer. High heat within the autoclave sterilizer literally bakes the unremoved contaminants onto the medical and dental instruments which may cause the instruments to be non-usable.

It is therefore an object of the invention to provide a hydro impact medical and dental instruments and other armamentarium washer which eliminates the need for hand scrubbing of dental and medical instruments.

It is also an object of the present invention to provide a medical and dental instruments washer which uses non-hazardous and relatively inexpensive cleaning solutions thereby eliminating the need for expensive hazardous cleaning solutions and their disposal.

It is also an object of the present invention to minimize or possibly eliminate the handling of contaminated medical and dental instruments so that the instruments need not be touched by personnel after use until they are completely cleaned and sterilized.

Another object of the present invention is to decrease the risk of instrument puncture wounds to those who handle medical and dental instruments for the purpose of cleaning and sterilizing this equipment.

It is another object of the present invention to decrease office overhead by minimizing the expenses currently associated with specialized ultrasonic cleaners and solutions, including their disposal.

SUMMARY OF THE INVENTION

The present invention avoids the foregoing problems in the prior art and achieves all the objects of the present invention by providing a hydro impact medical and dental instruments and other armamentarium washer capable of eliminating any tissue or contaminants which have accumulated on used medical and dental instruments so that the instruments are completely clean when placed in the autoclave or other sterilization device.

In accordance with the present invention, the hydro impact medical and dental instruments washer contains a housing having a water tight wash chamber for holding a fluid cleaning solution; a means for creating a continuous stream of liquid cleaning solution such that the continuous stream is of a defined cross sectional area within the housing; a means for supporting the medical and dental instruments; and a means for recirculating liquid cleaning solution within the wash chamber and for creating a velocity of the continuous stream of liquid cleaning solution sufficient to completely remove organic debris from medical and dental instruments. The washer may also have the recirculation means located outside of the wash chamber, an outlet means for allowing the solution to flow from the recirculation means to the wash chamber, and an inlet means for allowing the solution to flow from the wash chamber to the recirculation means. The washer may also include a means for providing heated cleaning solution within the wash chamber.

The means for creating a velocity of the continuous stream of liquid cleaning solution sufficient to completely remove organic debris from medical and dental instruments is typically a pump and he means for providing heat a heating element. The system may also contain a drain means for removing fluid from the wash chamber, a heat sensing means for monitoring the temperature within the wash chamber, and/or a means for directing fluid flow from the wash chamber toward the inlet flow means. The drain means may contain a valve to prevent fluid from escaping therefrom.

The present invention may also be summarized as a pre-sterilization hydro impact medical and dental instruments and other armamentarium washer having a housing with a watertight wash chamber therein; a means for recirculating liquid cleaning solution through the wash chamber at a flow rate sufficient to completely remove organic debris from a plurality of medical and dental instruments within the wash chamber; an outlet means for allowing liquid cleaning solution to flow into the wash chamber from the means for recirculating liquid cleaning solution, a means for supporting medical and dental instruments within the wash chamber, the means being capable of allowing liquid cleaning solution to flow therethrough; and an inlet means for allowing liquid cleaning solution to flow from the wash chamber to the means for recirculating liquid cleaning solution. The outlet means is of a sufficient cross sectional area to allow velocity and flowrate of liquid cleaning solution therethrough into the wash chamber which is sufficient to completely remove organic debris from a plurality of medical and dental instruments within a wash chamber. The inlet means is of a sufficient cross sectional area to allow a flowrate and velocity of liquid cleaning solution therethrough from the wash chamber thereby allowing the flowrate of liquid cleaning solution through the wash chamber to be sufficient to completely remove organic debris from a plurality of medical and dental instruments within the wash chamber.

The means for supporting the instruments may comprise a screen in the wash chamber, or a set of flanges oriented to support a basket having medical and dental instruments or other armamentarium therein. The means for supporting the instruments may alternatively comprise a rotatable basket which may be mounted on axles within the wash chamber. The flow of cleaning fluid through the wash chamber causes the basket to rotate on the axles within the wash chamber.

The system may also contain a timing switch to deactivate the recirculation means after a preset period of time.

To optimize cleaning efficiency of the system, it is preferred that the wash chamber have a cross sectional area substantially identical to the cross sectional area of the outlet means. This allows for optimum cleaning by increasing the amount of cleaning fluid which comes into contact with the instruments and also increasing the velocity at which the cleaning fluid circulates through the system. The wash chamber may comprise more than one area within which medical and dental instruments can be supported. These wash areas may be connected in series, such as a loop pattern, so long as the velocity of the cleaning fluid can be maintained throughout the system. The wash areas may also be connected in a manifold pattern wherein each section basket containing instruments to be cleaned.

It is most advantageous if the instruments placed within the wash chamber of the subject invention are placed in a position with the same axial direction as the flow of fluid through the wash chamber. This allows the cross sectional area of the wash chamber to be decreased which results in increased efficiency of use of the cleaning fluid. It is also important that the instruments be placed within the wash chamber so that one instrument does not block the circulation of the cleaning fluid to the next instrument within the wash chamber. This can be accomplished by placing the instruments in the same axial direction as the flow of fluid, and also by placing the instruments within a holding means which provides individual compartments or sections for placement of instruments. In the latter embodiment, the basket itself keeps the instruments from contacting one another and blocking flow to other instruments.

One advantage of the present invention is that the medical and dental instruments washer is capable of holding within the wash chamber a wire mesh basket which can then be placed within a sterilizer. Therefore, the instruments can be washed under high velocity within the apparatus, and subsequently the entire basket may be removed and placed within a sterilization device. In this manner, the medical and dental instruments do not need to be touched thereby increasing safety and minimizing the risk to office personnel.

BRIEF DESCRIPTION OF THE DRAWINGS

These and other objects, features and advantages of this invention will be evident from the following detailed description of several embodiments when read in conjunction with the accompanying drawings, where like reference numerals indicate like structures, in which.

contain significant "dead areas". However, when these wash chambers are filled with a liquid cleaning solution, if the velocity of fluid flowing into the wash chamber from the outlet means 4 is sufficient, the medical and dental instruments within an instrument cassette or basket 19 may be washed clean.

EXAMPLE 1

Referring to FIGS. 1-4, an embodiment of the washer includes a housing 1 preferably made of plastic material which encases various components. Within the housing there is the water tight internal wash chamber 2 for holding a fluid cleaning solution therein. The pump 3 is located outside the internal wash chamber 2 but within the housing 1. The outlet means 4 is connected from the discharge outlet 5 of the pump 3 to the internal wash chamber 2 while the inlet means 6 is connected from the wash chamber 2 to the inlet portion 7 of the pump.

The wash chamber 2 contains the means for supporting the medical and dental instruments therein.

A means for providing heat to within the wash chamber, typically a heating element 22, is located within the wash chamber along with a heat sensor 8 to monitor the temperature of the cleaning solution which is placed within the wash chamber 2. A drain 9 is located at the bottom of the wash chamber 2 for eliminating the cleaning solution that has been used within the wash chamber. A valve 26 is connected to the drain means via a conduit.

A water tight cover 10, which acts as a door is hinged 11 onto the wash chamber at one end and is clamped or latched on the other end to prevent any cleaning solution from escaping from the wash chamber while the apparatus is in operation. The latches 12 are provided to secure the cover to the housing and prevent cleaning solution from escaping from the wash chamber when the cover is closed. As a safety feature, a shut-off switch 13 is located between the cover 10 and the housing 1 at the hinged end 11 to deactivate the pump 3 when the cover is opened. With this feature, the pump can never be activated while the cover is open.

The pump is driven by an electric motor 14 which has a power lead 15 that runs through the housing 1 so that it can be plugged into a typical wall outlet. The pump 3 and motor 14 must be of sufficient power and capacity to provide a high velocity fluid flow within the wash chamber 2 so that medical and dental instruments placed therein will be washed clean. It has been found that a motor of the size between one and two horsepower will be sufficient for such operation. Preferably, a one horsepower motor with the capability of pumping approximately 87 gallons per minute of water will suffice for a portable washer. This size motor and pump operates on conventional 110-120 volt single phase power so that no special wiring is required to run the apparatus. It is apparent, however, that other sizes of pumps and motors may be utilized and preferred for different applications. For example, a washer designed to accommodate hundreds of instruments may be equipped with a larger capacity pump, motor and wash chamber.

The electric motor 14 drives the pump 3 which circulates the cleaning solution within the wash chamber 2 at high velocity. A typical impeller type pump is usable within the present invention. Plastic impeller pumps, because of their light weight and resistance to corrosion, are preferred. However, pumps having other types of impellers may also be used. The outlet means 4 is provided on a fluid flow connection 16 from the discharge of the pump to the wash chamber.

Similarly, the inlet 6 means is provided on a fluid flow connection 17 from the wash chamber to the inlet portion 7 of the pump. The inlet means 6 is preferably located at the bottom portion of the wash chamber downstream from the outlet means 4 so that fluid flows from the outlet 4 into the inlet 6 to the pump. It is preferred that the outlet 4 and inlet 6 means are located in position within the wash chamber which allow the fluid cleaning solution to naturally flow downstream from the outlet to the inlet. Such a configuration provides for an apparatus which produces optimal cleaning results. Alternatively, the inlet means could be located at a place within the wash chamber which is not naturally downstream of the flow, in such a case it may be preferable to include a means for directing fluid to flow from the outlet 4 to the inlet 6. Such a means could comprise a baffle plate or series of baffle plates (not shown). Also, the inlet may be equipped with a screen to prevent small instruments and debris from entering the inlet due to the force of the pump.

The outlet 4 and inlet 6 means must be sealed to the wash chamber 2 to prevent cleaning solution from leaking into the portion of the housing containing the motor and pump. Such a sealing means may include high quality caulking seal such as silicone, or a conventional gasket or rubber O-ring seal or any other acceptable material. The outlet and inlet means may have a flange located within the wash chamber and an O-ring supported by the flange. The outlet and inlet means may also be threaded on the inside to engage a typical slip joint nut, which when tightened will in combination with the O-ring provide a water tight seal. Alternatively, the outlet and inlet means may thread into an opening within the wash chamber or may be a one piece combination with the wash chamber wall. Many different sealing means will suffice. However, because of the high pressure and velocity of fluid discharging from the outlet means, the sealing system must be capable of withstanding high pressure fluids without leaking.

The cover 10 may contain a plurality of latches 12 which prevent the cover from being opened due to the force of the solution recirculated within the wash chamber 2. A seal 25 is located at the edge of the cover to engage the top edge of the housing 1. The combination of the seal 25 and latches 12, when tightened, will prevent solution from leaking from the wash chamber 2 when the pump 3 is activated.

In order to maintain a high velocity fluid flow within the wash chamber and to maximize pump efficiency, the flow area of the outlet means 4 is preferably greater than or equal to the flow area of the inlet means 6. These flow areas may also be equal in order to provide an optimum velocity outlet flow rate. In the preferred embodiment, the cross sectional area of the outlet opening 4 and the inlet opening 6 are identical. This relationship is largely responsible for creating a high velocity, violently turbulent flow within the wash chamber which removes tissue, contaminants and debris from the medical instruments.

Figure 1:
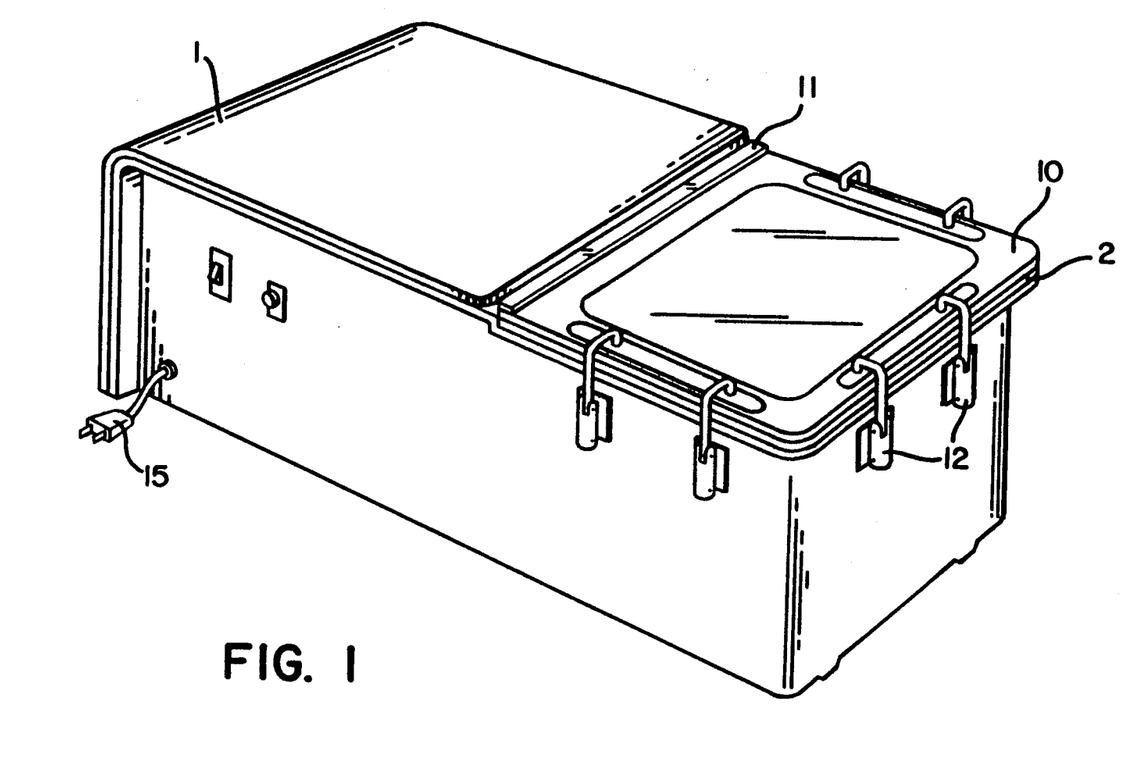
FIG. 1 is a perspective view of one embodiment of the hydro impact medical and dental instruments washer of the subject invention.
Figure 2:
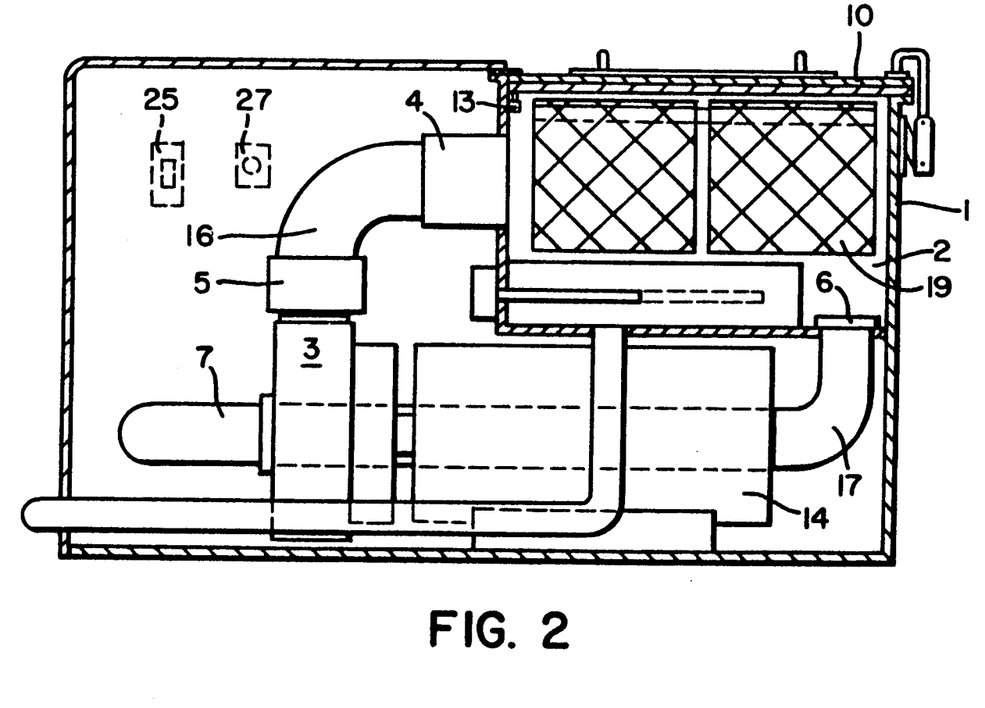
FIG. 2 is a sectional view from the side of the hydro impact medical and dental instruments washer shown in FIG. 1.
Figure 4:
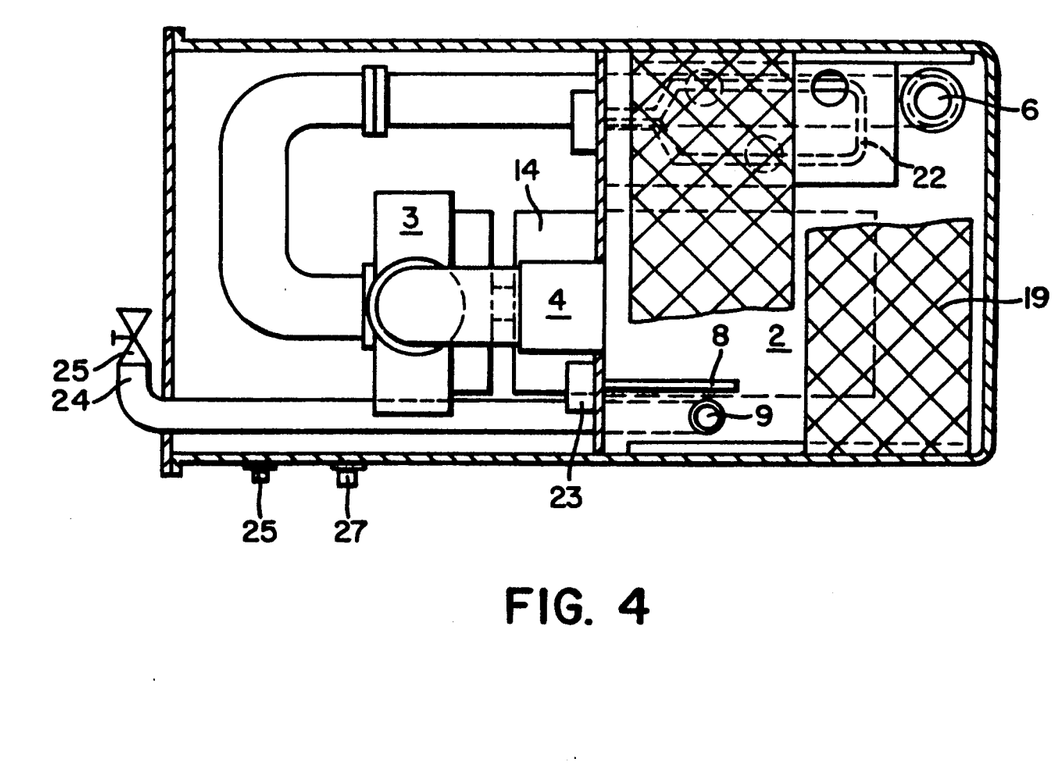
FIG. 4 is a sectional view from the top of the hydro impact medical and dental instruments washer shown in FIG. 1.

Support ridges 18 may be located at the upper portion of the wash chamber to hold or support a wire basket 19 designed to fit within the wash chamber as well as a sterilization device. As shown in FIGS. 2 and 4, the preferred embodiment may have a wash chamber capable of holding multiple wire baskets. The support ridges

DESCRIPTION OF THE PREFERRED EMBODIMENTS

Figure 8:
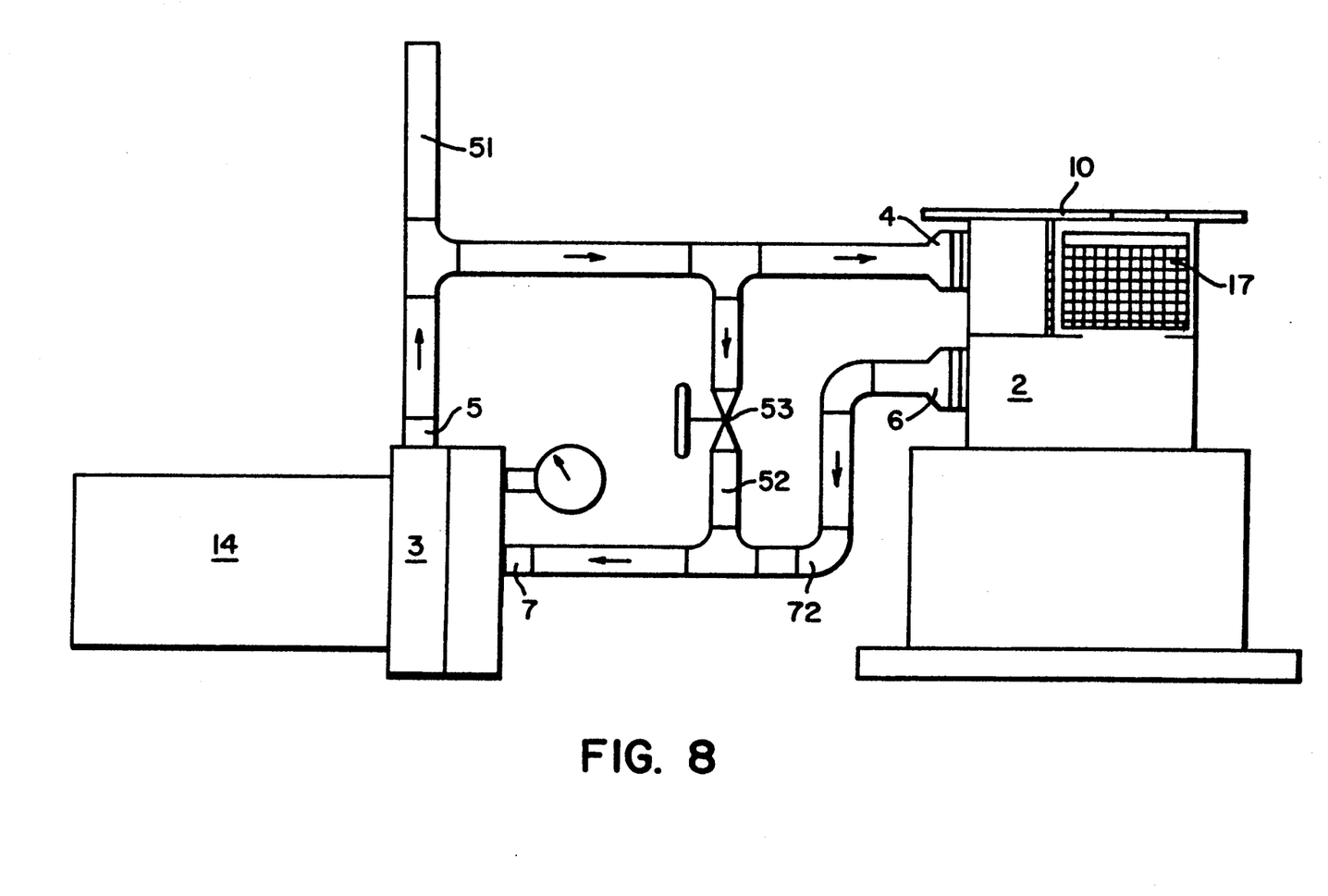
FIG. 8 is a schematic representation of the hydro impact medical and dental instruments washer in accordance with the principles of the present invention.

Referring to the FIG. 8, there is illustrated a schematic representation of a hydro impact medical and dental instruments washer in accordance with the principles of the present invention. The washer may be portable. The preferred embodiment encompasses a portable medical and dental instruments washer. However, the washer may be constructed of various sizes for the purpose of handling larger or smaller capacities of instruments.

The apparatus includes a pump 3 which is connected to a wash chamber 2 to allow fluid to be pumped into the wash chamber by the pump. The pump contains a discharge outlet 5 which is mounted in fluid flow relationship with an outlet means 4 connected to the wash chamber 2. An inlet means 6 is also connected to the wash chamber 2 and in fluid flow relationship with an inlet portion 7 of the pump. Accordingly, when the pump is activated, fluid flows from the discharge outlet 5 of the pump 3 through the outlet means 4 into the wash chamber and through the inlet means 6 and into the inlet portion 7 of the pump 7 where it is recirculated. The washer may contain an air hammer relief pipe 51 to allow air trapped within the system to escape therethrough and/or a by-pass line 52 having a gate valve 53 therein to control fluid flowing through the wash chamber 2.

The wash chamber is preferably configured so that fluid entering the wash chamber 2 from the discharge outlet 4 will flow through a means for supporting medical and dental instruments, such as an instrument cassette or wire basket 19 and into the inlet means 6. This is most easily accomplished by constructing a wash chamber 2 which is shaped such that fluid must flow from the discharge outlet 4 within and through the instrument cassette or basket 19, over the medical and dental instruments, and through the inlet means 6 where it will be recirculated again through the wash chamber by the pump 3. Accordingly, it is necessary that the means for supporting medical and dental instruments such as the instrument cassette or basket 19 allow cleaning fluid such as a liquid cleaning solution to flow therethrough does not facilitate the flow of liquid cleaning solution from the outlet means over the medical and dental instruments within the instruments cassette or wire basket 19.

The pump must be capable of creating a flowrate of liquid cleaning solution which will be sufficient to completely remove organic debris from a plurality of medical and dental instruments within the wash chamber. The conduits 71, 72 leading to and from, respectively, the wash chamber must also be of a sufficient cross sectional area to allow the flowrate of liquid cleaning solution being pumped therethrough to be sufficient to create a velocity and flowrate of liquid cleaning solution through the wash chamber 2 which is sufficient to remove organic debris from a plurality of medical and dental instruments within the wash chamber. Also, the inlet means 6 should be of a sufficient cross sectional area to allow a flowrate of liquid cleaning solution therethrough from the wash chamber 2 which allow the velocity and flowrate of liquid cleaning solution through the wash chamber to be sufficient to completely remove organic debris from the medical and dental instruments therein. The means for supporting medical and dental instruments within the wash chamber should be capable of allowing liquid cleaning solution to flow therethrough. The apparatus should be constructed so that the flowrate of liquid cleaning solution from the pump 3 to the wash chamber 2 and the wash chamber 2 to the pump 3 is sufficient to allow the flowrate of liquid cleaning solution through the wash chamber to be capable of allowing the liquid cleaning solution in the wash chamber to wash medical and dental instruments clean in a relatively short period of time. For example, if the outlet means 4 leading to the wash chamber is of a relatively small cross sectional area, the flowrate of fluid into the wash chamber 2 and through the wash chamber 2 will be insufficient to clean medical and dental instruments therein. Although the velocity of the fluid flowing from the outlet means into the wash chamber may be relatively high, the volume of fluid flowing therethrough may be insufficient to create a flowrate which is sufficient to clean medical and dental instruments in the wash chamber. Accordingly, fluid must flow through fluid carrying means, such as conduits which have a sufficient cross sectional area to allow the proper flowrate therethrough and into and through the wash chamber.

Preferably, conduits 71, 72 leading from the wash chamber to the pump and to the pump form the wash chamber are of identical cross sectional area. This is preferred so that the flowrate of fluid entering the wash chamber 2 is equal to the flowrate of fluid exiting the wash chamber and that the overall amount of liquid cleaning solution within the wash chamber does not increase or decrease significantly over a period of time. Under this condition in the pressure differential of fluid flowing out of the pump does not decrease significantly through its course of travel.

Superior cleaning results are obtained when the flow of fluid into the wash chamber 2 forms a continuous stream of liquid cleaning solution of a defined cross-sectional area and where the medical and dental instruments are placed within the defined cross-sectional area of the flow of liquid cleaning solution within the wash chamber. This may be achieved by having the fluid level within the wash chamber be above the outlet means, and having the cassette or wire basket 19 positioned such that the fluid flow from the outlet means flows through the cassette or wire basket. The medical and dental instruments will be within the defined cross sectional are of the stream of liquid cleaning solution flowing within the wash chamber. For example, the system which contains a high proportion of medical and dental instruments within the continuous stream of liquid cleaning solution having a defined cross-sectional area is depicted in the embodiment described herein in Example 3. It has been found that by virtue of the relationship between the cross-sectional area of the fluid flowing within the chamber and the medical and dental instruments placed within the cross-sectional area of the fluid flow, optimum cleaning results are achieved. This type of wash chamber configuration is deemed to have minimal "dead area" which may be defined as locations within the wash chamber where fluid is most stagnant such as vortices or wakes which may occur between corners or behind baffle plates, for example.

Although such a wash chamber configuration will obtain optimum cleaning results, other wash chamber configurations may be used. Although these wash chambers may not result in similar cleaning results, they may yield sufficient cleaning results. For example, the wash chambers referred to in Examples 2 and 3, infra, 18 extend throughout the length of the wash chamber 2. This feature enables personnel to place the wire basket within the wash chamber while the apparatus is not in use. After the instruments have been used, they can be placed within the basket. The apparatus may be activated immediately or later when the baskets are filled to capacity. After the machine has scrubbed the instruments clean, the entire wire basket may be removed from the wash chamber and placed directly in a sterilization unit where the instruments are then sterilized. Therefore, instruments are effectively cleaned and sterilized without being touched after they have been used. As an alternative to the support ridges, a screen may be located at the upper portion of the wash chamber. The screen could be mounted across the lower portion of the wash chamber 2. The wire basket 19 could be placed directly on the screen for convenience.

Figure 3:
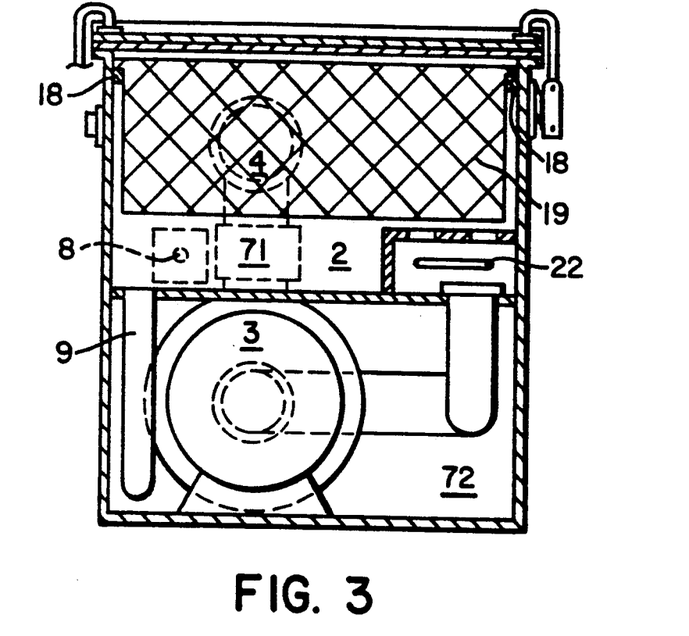
FIG. 3 is a sectional view from the end of the hydro impact medical and dental instruments washer shown in FIG. 1.
Figure 9:
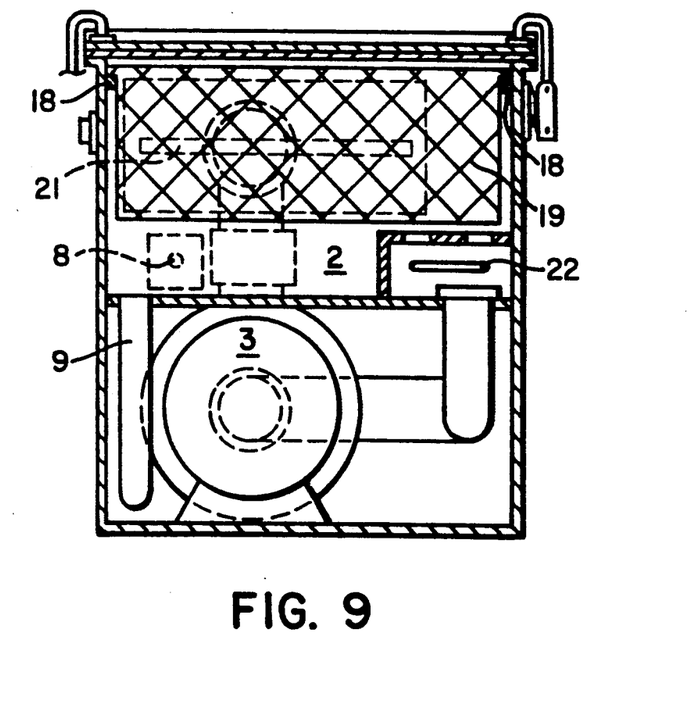
FIG. 9 is a sectional view from the end of the hydro impact medical and dental instruments washer of FIG. 1 having a horizontal passage at the outlet means.

The outlet means 4 may have various cross sectional configurations for dispersing the outlet flow into the wash chamber 2. The cross sectional configuration of the outlet means 4 should be coordinated with the orientation of the medical and dental instruments within the wire basket 19 so that fluid leaving the outlet means 4 has a defined cross sectional area which contacts the instruments within the basket. For example, the outlet means 4 may be shaped as a passage extending horizontally along the length of the basket 19 and the basket oriented to allow instruments to be set in a position, preferably, within the flow of a continuous stream of liquid cleaning solution from the passage. Various geometrical cross sectional configurations for the outlet means 4 may also be sufficient. For example, the outlet means 4 may be a circular cross-section which leads directly to the wash chamber 2, as shown in FIG. 3, or a horizontal passage which leads directly to the wash chamber, as shown in FIG. 9. The cleaning time associated with each type of outlet opening may vary accordingly.

The operating temperature of the cleaning solution within the wash chamber may be approximately 100° F. However, the heating element 22 may be set to activate up to a point where the water temperature reaches approximately 150°. In order to allow the system to more efficiently clean instruments, the heating element should be located within the wash chamber and be capable of heating the water to a temperature of at least 100°±. The heat sensor 8, also located within the wash chamber, monitors the temperature of the cleaning solution. The heat sensor 8 may be connected to a hot water control 23 which in response to the sensed temperature of the cleaning solution, will deactivate the heating element 22. The heat sensor 8 will sense the temperature of the cleaning solution and when the temperature reaches 150°±, or some other predetermined level, the heat sensor control 23 will shut off the heating element. Any heat sensor such as a thermometer or thermocouple and heat sensitive switch will suffice for the control for use in the present invention. Both the heating element 22 and hot water control 23 are preset so that the temperature of the cleaning solution may be run within the prescribed temperature ranges. It has been found that optimal cleaning results are achieved when the temperature of the cleaning solution remains above 100°± F. Preferably, the hot water control 23 causes the heating element 8 to activate when the cleaning solution temperature is less than 100°± F. and deactivate at 150°± F. so that the operating temperature is preferably kept between 100°±-150°± F. Although the aforementioned temperatures are representative of the temperature ranges which have been used successfully in the preferred embodiment, it is apparent that adequate cleaning results will be achieved at other temperatures as well.

A drain 9 may be located in the wash chamber to efficiently remove the cleaning solution after it has been used. This eliminates the need for lifting and tipping the apparatus in order to dispose of the used solution. The drain may contain a nipple 24 on which may be connected a drain hose so that the cleaning solution can be disposed directly into a drain.

The washer may be powered using conventional 110 single phase voltage. The motor is preferably activated through a ground fault interruption switch which provides a safety shut off means should there be a short, for example, due to the presence of water in the system. A switching relay (not shown) is also provided so that both the ground fault interruption switch 25 or the safety shut off switch 13 may control the electric motor. The apparatus may also contain a timer switch 27 to control the duration of the wash cycle. The timer switch 27 is connected to the relay so that when it is activated and time has expired, the pump motor is deactivated.

The medical and dental instruments and other armamentarium washer in accordance with the present invention is used by opening the cover 10 and filling the wash chamber 2 with a cleaning solution so that it is substantially filled. The chamber is preferably filled to a level where the instruments are submerged when the pump is not activated. and the outlet means 4 is below the fluid level to prevent air from being pumped through the system.

One preferred cleaning solution is ULTRA ™ (Klenzade, Ecolab Research Center, St. Paul, Mn.). ULTRA ™ is a non foaming, chlorinated, alkaline cleaner which is preferably used at a concentration of one ounce per two gallons of water. This alkaline cleaner has no foam characteristics and successfully cleans stainless steel equipment. The chlorine in the product is very useful in breaking down organic soils, particularly proteins such as may be present from tissues or blood on medical or dental instruments. However, other commercially available cleaning solutions may be used.

Medical and dental instruments are then placed in the basket or cassette 19 which is placed within the wash chamber 2 on the support means 18. The cover 10 must then be closed and the latches 12 tightened to prevent solution leaking from the wash chamber. When the switch 25 is activated, water circulates from the wash chamber into the inlet means 6 through the pump 3 and through the outlet means 4 into the wash chamber. The fluid is capable of being recirculated within the system until the cleaning cycle is completed. A violently turbulent flow is created within the wash chamber enabling medical and dental instruments and armamentarium which have dried residue, contaminants and tissue thereon to be washed clean within a few minutes. It has been found that medical and dental instruments have been washed completely clean in as low as three minutes wash time. After the cleaning cycle has been completed, the instruments are removed from the wash chamber. The cleaning solution may be discarded or, if reusable, may be reused in other cleaning cycle.

EXAMPLE 2

Figure 5:
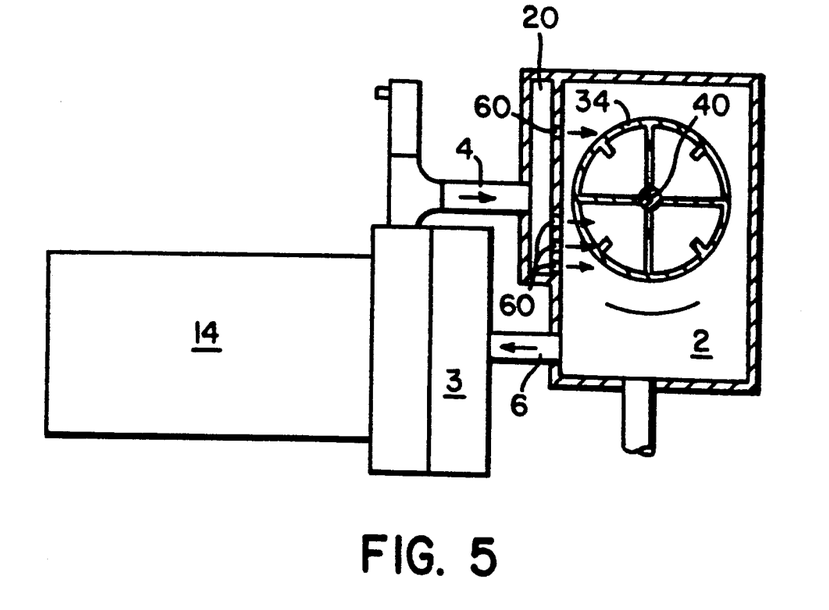
FIG. 5 is a schematic representation of a further embodiment of a hydro impact medical and dental instruments washer of the subject invention.

Referring to FIG. 5 there is illustrated another preferred embodiment of a hydro impact medical and dental instruments washer. In this embodiment, an electric motor 14 drives the pump 3 which circulates the cleaning solution within the wash chamber 2 at high velocity. The cleaning solution enters the wash chamber 2 at the outlet means 4 of the pump and exits the wash chamber 2 at the inlet means 6 to the pump 3. This embodiment differs from that previously discussed in that the medical and dental instruments are placed in a freely rotating basket 34. The cylindrical basket 34 may have internal hydraulic motor plates (not shown) which also agitate the instruments to effect cleaning. The basket 34 is allowed to rotate within the wash chamber 2 by mounting it on end axles 40 within the wash chamber 2. Cleaning fluid is allowed to flow through the basket 34 which is made of a mesh material to allow the liquid cleaning solution to flow therethrough.

The outlet means 42 and discharge head 20 may be configured in such a manner which allows the fluid discharged therefrom to vary along the length of the discharge head. This may be achieved by varying the cross sectional area of the discharge head 20 along its length or by providing a plurality of ports 60 along the length such that more ports 60 are located at one end of the discharge head. The variation in flow will cause the force of the fluid impacting the rotatable basket 34 to also vary (along the diameter of the basket) thereby causing the basket 34 to rotate. Such a discharge head is not necessary, however, and other configurations for outlet means 4 such as that depicted in Example 1 may suffice.

EXAMPLE 3

Figure 6:
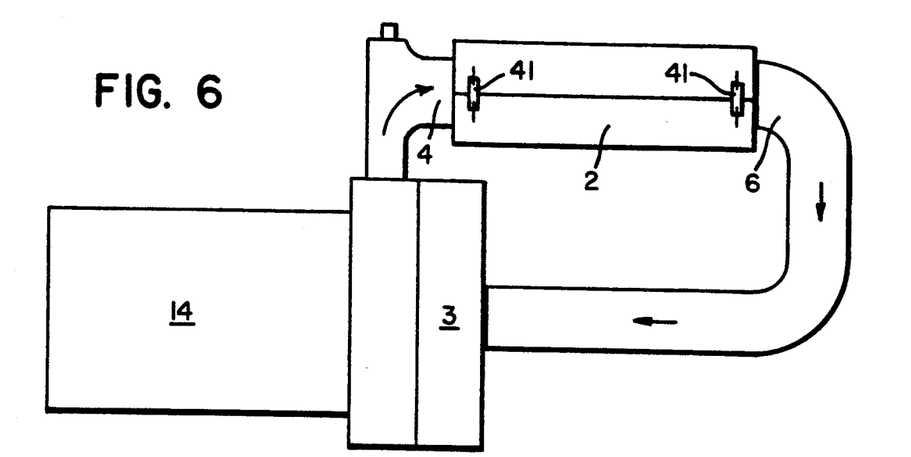
FIG. 6 is a schematic representation of a further embodiment of a hydro impact medical and dental instruments washer of the subject invention.

Referring to FIG. 6 there is illustrated another embodiment of a hydro impact medical and dental instruments washer which achieves optimal cleaning results. In this embodiment the electric motor 14 also drives the pump 3 which circulates the cleaning solution within the wash chamber 2 at high velocity. The cleaning solution enters the wash chamber 2 at the outlet means 4 of the pump 3 and exits the wash chamber 2 by the inlet means 6 to the pump 3.

In this embodiment, the cross sectional area of the wash chamber 2 is substantially the same as the cross sectional area of the outlet 4 and inlet 6. By minimizing the cross sectional area of the wash chamber 2, the percentage of cleaning fluid utilized during the wash cycle which contacts the instruments placed within the wash chamber 2 is increased. The instruments will be completely within the defined cross sectional area of the stream of liquid cleaning solution within the wash chamber 2. Preferably, the wash chamber should allow fluid to flow therethrough at a maximum possible velocity while also allowing the circulating fluid to contact the maximum area of the instruments. This results in a more efficient cleaning because of the increased amount of cleaning fluid which comes into contact with the medical and dental instruments. This minimized cross sectional area of the wash chamber 2 also results in maximum velocity flow through the wash chamber 2. This maximum fluid velocity and maximum contact between the flow of cleaning fluid and the medical and dental instruments allows for optimum cleaning thereby resulting in more efficient cleaning of the medical and dental instruments. The configuration of the wash chamber eliminates any dead areas.

Figures 7A, 7B, 7C, 7D:
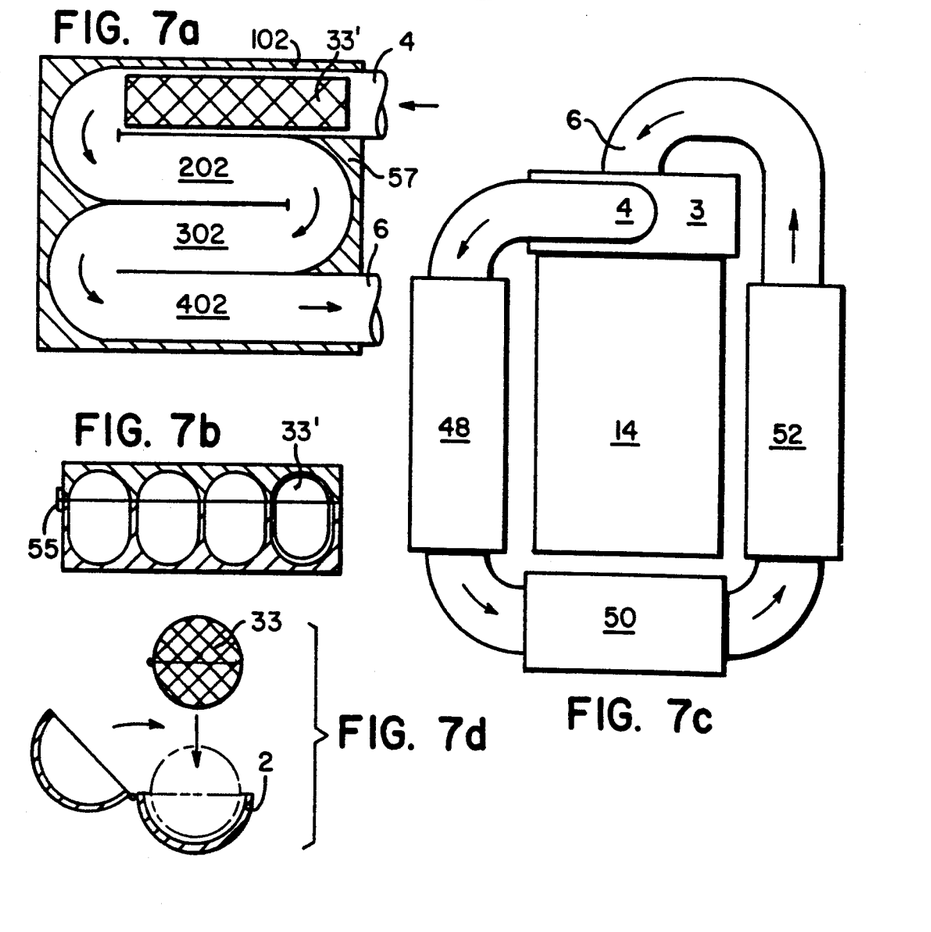
FIGS. 7A is a top view of a wash chamber having a manifold for insertion of instrument cassettes.
FIG. 7B is a side view of the manifold shown in FIG. 7A.
FIG. 7C is a top view of a hydro impact medical and dental instruments washer of the subject invention having several wash chambers in series connected to a single pump.
FIG. 7d is a cross sectional view of the wash chamber with the manifold open for insertion of instrument cassettes.

In this embodiment, the wash chamber comprises a top and a bottom portion connected by hinges 41, allowing the top portion of the wash chamber 2 to be opened in order to insert an instrument holding means such as cassettes 33 or wire mesh baskets which may contain the medical and dental instruments (FIG. 7d). Preferably, the instruments are placed within the wash chamber 2 in the same axial direction as the flow of cleaning solution coming from the outlet 4. The means for supporting the instruments should be configured to allow the flow of cleaning fluid therethrough and to allow the instruments to be placed in the same axial direction as the fluid flow. For example, the cassette 33 shown in FIG. 7d will suffice. Moreover, the instrument holding means may be configured to allow separation of the individual instruments when placed therein. By placing the instruments, which generally have a length which exceeds their width, in the same axial direction as the flow of cleaning fluid through the wash chamber 2, one is enabled to make the wash chamber of a cross sectional area similar to the outlet 4 and inlet. The benefits of such a cross sectional area are discussed above.

Preferably, the instruments are placed within the wash chamber 2 so that the axial flow of fluid does not cause any instrument to block the contact of any other instrument with the fluid. This can be accomplished by placing the instruments within separate sections within the instrument holding cassette 33 placed within the wash chamber 2. Otherwise, if the instruments are placed perpendicular to the axial direction of flow, one instrument effectively blocks the contact of the next instrument with the cleaning solution. This can also be overcome by placing the instruments in the same axial direction as the flow of cleaning solution.

EXAMPLE 4

Referring to FIGS. 7A–7C, there are illustrated additional embodiments of a hydro impact medical and dental instruments washer of the subject invention. As shown in FIG. 7A, an outlet means 4 provides the flow of fluid from a pump (not shown). The fluid flows through a manifold containing a wash chamber 2 divided into a plurality of sub chambers 102, 202, 303, 402 and exits at the inlet means 6, returning the circulating wash fluid to the pump.

Numerous wash chambers can be provided utilizing this manifold pattern, and each chamber provides an area into which an instrument holding means such as a cassette 33 (or wire cage) can be inserted. As shown in FIG. 7A, four chambers may be provided. However, the number of chambers is not limited thereto. A cassette 33, useable as the instrument holding means, is inserted into channel 47 and similar cassettes could be inserted into each of the other sub chambers. The cassette 33 or similar instrument holding means may comprise any suitable instrument holder which will allow the instruments to be axially oriented therein while allowing the flow of cleaning solution therethrough to contact the instruments. The instrument holding means may contain various clips or other components which allow instruments to be secured therein.

The manifold arrangement of the wash chambers includes a top connected by a hinge 55, as best shown in FIG. 7B. This hinged top can be opened, allowing access to all four sub chambers, by opening one lid to the wash chamber. This allows for the insertion of four instrument holding means within the chambers much more easily than if each of the chambers were provided with their own separate openings.

FIG. 7C illustrates an additional arrangement of multiple wash chambers, each similar to that shown in FIG. 6, connected in series each having an instrument holding means therein wherein the pump 3 circulates the cleaning fluid through the outlet means 4. Then the cleaning fluid returns to the pump via inlet means 6. Within each wash chamber, 48, 50 and 52, a cassette 33 can be inserted. This system differs from the manifold arrangement shown in FIG. 7A in that each wash chamber, 48, 50 and 52, is accessible via its own opening or top.

It should be readily apparent that in the manifold arranged or the loop arrangement, any number of individual sub chambers, or wash chambers, can be connected in series depending upon the fluid pumping capacity necessary for washing. It is only necessary that the velocity of the fluid flow provided by the pump be satisfactory to maintain velocity throughout the manifold and loop patterns.

As in the embodiment shown in FIG. 6, the cross sectional area of the was chambers is substantially identical to the cross sectional are of the outlet 4 and inlet 6 (FIG. 7A) and the outlet 44 and inlet 46 (FIG. 7C. In these embodiments shown in FIG. 7A-7C it is also preferable to place the instruments within the wash chambers in the same axial direction of flow as the cleaning fluid.

Although the embodiments described herein are portable medical and dental instruments and armamentarium washer, the invention is not limited to a portable model. The washer may be permanently installed within an office or hospital, may include permanent plumbing for the supply and drainage of water, and may be equipped with a large capacity pump or pumps as well as large capacity wash chambers.

It is evident that the invention may be embodied in a variety of ways differing from those described herein, but without departing from the scope of the invention as defined by the claims. Various different modifications other than those described herein may be made to the system. Any such modifications are intended to be included within the spirit of the invention and scope of the claims.

We claim:

1. A pre-sterilization hydro impact medical and dental instruments and other armamentarium washer comprising:

a housing having a water tight wash chamber therein fillable with a liquid cleaning solution, an inlet leading thereto and an outlet leading therefrom;

means for creating a continuous stream of liquid cleaning solution through said wash chamber wherein the continuous stream of liquid cleaning solution is of a defined cross-sectional area within the housing;

means for supporting medical and dental instruments within said defined cross-sectional area, said means being capable of allowing the continuous stream of liquid cleaning solution to flow therethrough; and means for recirculating the liquid cleaning solution through said wash chamber and for creating a velocity and flow rate of said continuous stream of liquid cleaning solution sufficient to completely remove organic debris from medical and dental instruments within said defined cross-sectional area wherein the wash chamber is capable of being substantially filled with liquid cleaning solution and the means for recirculating the liquid cleaning solution activated to wash the medical and dental instruments clean wherein the wash chamber, the inlet and outlet of the wash chamber, and the means for recirculating the liquid cleaning solution have substantially identical cross sectional areas to allow said recirculating means to generate a velocity and flow rate of liquid cleaning solution within the wash chamber sufficient to completely remove organic debris from medical and dental instruments.

2. The hydro impact medical and dental instruments and other armamentarium washer of claim 1 wherein said means for creating a continuous stream of liquid cleaning solution of a defined cross sectional area comprises an outlet means for allowing solution to flow from the recirculation means to the wash chamber and an inlet means for allowing solution to flow from the wash chamber to the recirculation means.

3. The hydro impact medical and dental instruments and other armamentarium washer of claim 2 wherein the means for recirculating the liquid cleaning solution and for creating a velocity and flow rate of said continuous stream of liquid cleaning solution sufficient to completely remove organic debris from medical and dental instruments further comprises a pump connected between said inlet and said outlet means of said means for creating a continuous stream of liquid cleaning solution.

4. The hydro impact medical and dental instruments and other armamentarium washer of claim 3 wherein the means for supporting the medical and dental instruments further comprises a mesh basket housing medical and dental instruments therein.

5. The hydro impact medical and dental instruments and other armamentarium washer of claim 4 wherein the means for supporting instruments in the wash chamber comprises a set of flanges oriented to support the mesh basket.

6. The hydro impact medical and dental instruments and other armamentarium washer of claim 3 comprising one or more wash chambers connected in series.

7. The hydro impact medical and dental instruments and other armamentarium washer of claim 6 wherein said wash chamber comprises a manifold having a wash chamber divided into a plurality of sub chambers therein.

8. The hydro impact medical and dental instruments and other armamentarium washer of claim 6 wherein the wash chambers are connected in a loop pattern.

9. The hydro impact medical and dental instruments and other armamentarium washer of claim 1, wherein said means for supporting medical and dental instruments further comprising an instrument holding means for allowing instruments to be axially oriented within the wash chamber and for allowing a liquid cleaning solution to flow therethrough and contact the instruments.

10. The hydro impact medical and dental instruments and other armamentarium washer of claim 7 wherein the washer is portable.

11. The hydro impact medical and dental instruments and other armamentarium washer of claim 4 further comprising:

means for providing heated liquid cleaning solution within the wash chamber.

12. The hydro impact medical and dental instruments and other armamentarium washer of claim 4 further comprising a drain means for removing fluid from the wash chamber.

13. The hydro impact medical and dental instruments and other armamentarium washer of claim 12 further comprising a heat sensing means for monitoring the temperature within the wash chamber.

14. The hydro impact medical and dental instruments and other armamentarium washer of claim 13 wherein the means for providing heat to within the wash chamber comprises a heating element within the wash chamber.

15. The hydro impact medical and dental instruments and other armamentarium washer of claim 4 further comprising a timing switch means for deactivating the pump after a preset period of time.

16. A pre-sterilization hydro impact medical and dental instruments and other armamentarium washer comprising:
a watertight wash chamber having an outlet means leading thereto and an inlet means leading therefrom, said wash chamber having a means for supporting medical and dental instruments therein;
means for recirculating liquid cleaning solution through the wash chamber at a velocity and flow rate sufficient to completely remove organic debris from medical and dental instruments within said chamber, said recirculating means having an inlet portion leading thereto and an outlet portion leading therefrom; and
wherein said wash chamber, outlet portion and inlet portion have substantially identical cross sectional areas to allow said recirculating means to generate a velocity and flow rate of liquid cleaning solution within the wash chamber sufficient to completely remove organic debris from medical and dental instruments wherein medical and dental instruments within the wash chamber are washed clean when said recirculation means is activated.

17. A pre-sterilization hydro impact medical and dental instruments and other armamentarium washer comprising:
a watertight wash chamber;
means for recirculating liquid cleaning solution through the wash chamber at a velocity and flow rate sufficient to completely remove organic debris from medical and dental instruments within the wash chamber, said recirculating means having an inlet leading thereto and an outlet leading therefrom;
means for allowing liquid cleaning solution to flow into the wash chamber from the means for recirculating liquid cleaning solution, said means for allowing liquid cleaning solution to flow being of sufficient cross sectional area to allow a velocity and flow rate of liquid cleaning solution into the wash chamber sufficient to completely remove organic debris from a plurality of medical and dental instruments within the wash chamber;
means for supporting medical and dental instruments within the wash chamber; and
means for allowing liquid cleaning solution to flow from the wash chamber to the means for recirculating liquid cleaning solution, said means for allowing liquid cleaning solution to flow from the wash chamber to the means for recirculating liquid cleaning solution, said wash chamber and said inlet of the recirculating means having substantially identical cross sectional areas to allow said recirculation means to generate a flow rate of liquid cleaning solution through the wash chamber sufficient to completely remove organic debris from medical and dental instruments within the wash chamber.

18. A pre-sterilization hydro impact medical and dental instruments and other armamentarium washing process comprising:
creating a continuous stream of liquid cleaning solution through a housing having a water tight wash chamber therein fillable with said liquid cleaning solution wherein the continuous stream of liquid cleaning solution is of a defined cross sectional area within the wash chamber;
supporting medical and dental instruments within said defined cross-sectional area while allowing the continuous stream of said liquid cleaning solution to flow through the wash chamber; and
recirculating the liquid cleaning solution through said wash chamber at a velocity and flow rate sufficient to completely remove organic debris from the medical and dental instruments within said defined cross-sectional area using a recirculating means.

19. The process of claim 18 wherein recirculating the liquid cleaning solution is accomplished by pumping liquid cleaning solution from an inlet means of said recirculating means leading from said wash chamber and through an outlet means of said recirculating means leading into said wash chamber.

20. The process of claim 19 further comprising supporting the medical and dental instruments axially within the defined cross-sectional area.

21. The process of claim 19 wherein creating said continuous stream of liquid cleaning solution through said wash chamber of the defined cross-sectional area is achieved by having a cross-sectional area of the wash chamber substantially identical to the cross-sectional area of the outlet means.

22. The process of claim 19 further comprising heating the liquid cleaning solution.

23. The process of claim 19 further comprising supporting medical and dental instruments within said defined cross-sectional area by using an instrument holding means capable of allowing the liquid cleaning solution to flow therethrough and contact the medical and dental instruments.

* * * * *